United States Patent [19]
Cook et al.

[11] Patent Number: 5,981,738
[45] Date of Patent: *Nov. 9, 1999

[54] UV CURABLE CELLULOSE ESTERS

[75] Inventors: Phillip Michael Cook, Kingsport; Robert Andrew Simm, Mt. Carmel, both of Tenn.

[73] Assignee: Eastman Chemical Company, Kingsport, Tenn.

[ * ] Notice: This patent is subject to a terminal disclaimer.

[21] Appl. No.: 09/132,442

[22] Filed: Aug. 11, 1998

Related U.S. Application Data

[63] Continuation of application No. 08/877,357, Jun. 17, 1997, Pat. No. 5,871,573, which is a continuation of application No. 08/558,995, Nov. 16, 1995, Pat. No. 5,741,901.

[51] Int. Cl.$^6$ .............................. C08B 3/22; C08G 63/00
[52] U.S. Cl. .............................. 536/76; 536/69; 527/311; 527/313; 527/314; 526/238.2; 526/233.21
[58] Field of Search ....................... 536/76, 69; 527/311, 527/313, 314; 526/238.2, 238.21

[56] References Cited

U.S. PATENT DOCUMENTS

| | | | |
|---|---|---|---|
| 3,749,592 | 7/1973 | Gaske et al. | 536/56 |
| 4,112,182 | 9/1978 | Newland et al. | 536/56 |
| 4,147,603 | 4/1979 | Pacifici et al. | 536/56 |
| 4,490,516 | 12/1984 | Verbanac | 536/56 |
| 4,565,857 | 1/1986 | Grant | 536/56 |
| 4,758,645 | 7/1988 | Miyazano et al. | 527/311 |
| 4,839,230 | 6/1989 | Cook | 536/56 |
| 5,741,901 | 4/1998 | Cook et al. | 536/76 |

FOREIGN PATENT DOCUMENTS 2 159 524   12/1995   United Kingdom .

OTHER PUBLICATIONS

Chemical Abstracts, vol. 82, No. 12, 1975, Columbus OH, US; abstract No. 74706z, p. 96, col. left; XP002024819 & JP 49 026 943 A (Daicel LTD) Jul. 13, 1974.

Abstracts Bulletin of the Institute of Paper, 43(8) (Feb. 1973), p. 789, abstract N. 8122 & Uzbek. Khim. Zh. 15(5): 67–70 (1971) Kayumova Kh et al XP002024816.

Abstracts Bulletin of the Institute of Paper Chemistry, 52(10) (Apr. 1982), p. 1120, abstract N.10631 & Azerb. Khim. Zh., No. 6: 105–110 (1980) Alimardanov R. S. et al. XP002024817.

Abstracts Bulletin of the Institute of Paper Chemistry, 50(4) (Oct. 1979), p. 378, abstract N.3513(U) & USSR Pat. 659574, XP002024818.

Indian Journal of Pharmaceutical Science, vol. 49, No 1, 1987, pp. 1–4, XP000617988, Murthy R.S.R. et al: "Synthesis and evaluation of cellulose acetate malcate as an enteric coating agent".

*Primary Examiner*—Elli Peselev
*Attorney, Agent, or Firm*—Jonathan D. Wood; Harry J. Gwinnell

[57] ABSTRACT

The present invention relates to a modified cellulose ester containing unsaturated pendent groups which can be prepared by reacting a cellulose ester containing residual hydroxyl groups with, for example, maleic anhydride in acetic acid solvent with sodium acetate catalyst. The modified cellulose ester is not homopolymerizable but will copolymerize in the presence of vinyl crosslinking agents and a photoinitiator upon exposure to ultraviolet radiation. The modified cellulose ester is useful as a protective and/or decorative coating for wood, metal, plastics, paper, board, and other substrates, as well as an additive to printing inks, and as a nail polish. In addition, because of the propensity for the pendant carboxyl groups to form hydrophilic salts with amines, the modified cellulose esters can be formulated to be water-dispersible.

4 Claims, No Drawings

UV CURABLE CELLULOSE ESTERS

This is a Continuation application of application Ser. No. 08/877,357, now U.S. Pat. No. 587,573 filed Jun. 17, 1997, which is a Continutation of having a filing date of Ser. No. 08/538,995 Nov. 16, 1995 and U.S. Pat. No. 5,741,901.

FIELD OF THE INVENTION

This invention belongs to the field of polymer chemistry. In particular, this invention relates to certain cellulose ester derivatives which possess groups capable of free radical addition reactions with ethylenic groups on other compounds upon exposure to ultraviolet light in the presence of an initiator, thermally, or when exposed to electron beam radiation.

BACKGROUND OF THE INVENTION

Cellulose esters are used extensively in lacquer coatings because they are compatible with many resins and additives, they exhibit good gap-filling properties, they dry quickly, they can be sanded or rubbed soon after application, they exhibit low toxicity, and they form a very aesthetically-pleasing coating on a variety of substrates. Such coatings can be applied with reproducible results and can be repaired or even removed with the use of solvent. Such lack of solvent resistance is an advantage for lacquer handling since equipment used to apply the lacquer can be readily cleaned and the coating can be repaired easily if damaged. However, good solvent and stain resistance of the applied coating also is highly desirable, particularly if the coating is intended to be protective in nature. Moreover, cellulose ester lacquer coatings tend to be rather soft and are easily scratched.

Thermoset coatings have excellent solvent resistance and hardness properties, but they also have serious disadvantages. Most are thermally cured or crosslinked and their use is thus limited to substrates which are stable at the curing temperatures which can be as high as 230° C. Moisture-cured systems have been used to overcome the use of high cure temperatures but these have prolonged cure times and have humidity requirements for such curing. The use of ultraviolet radiation to transform a photocrosslinkable thermoplastic coating into a thermoset coating thus represents a potentially desirable improvement. Curing can occur over a period of seconds to yield a hard, stain-resistant coating. In this manner, the advantages of both thermoplastic and thermoset polymers can be maintained.

It is also highly desirable to limit the amount of solvent used to apply such coatings due to environmental and work exposure issues. The use of water dispersible resins and resins dissolved in reactive solvents represent two potential solutions.

Attempts have been made to prepare cellulose-based resins that seek to provide such desired coatings and methods of application; however, such attempts have major deficiencies. For example, U.S. Pat. Nos. 4,112,182; 4,490, 516; 3,749,592; and 4,147,603 do not provide crosslinkable resins having the desired level of solvent resistance and hardness, nor do any of these references teach the use of these resins in water dispersible or reactive solvent coatings.

Photopolymerizable cellulose esters described in U.S. Pat. No. 4,565,857 display a wide range of reactivities. For example, cellulose acetate propionate grafted with 2-isocyanatoethyl methacrylate per mole of anhydroglucose units has a short pot life in the presence of peroxides or a photoinitiator such as Ciba Geigy's IRGACURE® 651 Photocuring Agent (2,2-dimethoxy-2-phenylacetophenone) and can gel unexpectedly.

Other cellulose esters such as cellulose acetate propionate grafted with 0.9 moles of m-isopropyl-alpha, alpha-dimethylbenzyl isocyanate per mole of anhydro-glucose units completely fail to crosslink when exposed to UV radiation in the presence of a photoinitiator.

U.S. Pat. No. 4,839,230 describes grafted cellulose esters prepared by reacting a hydroxy-functional cellulose ester with an acrylic based compound and m-isopropenyl-α,α-dimethylbenzylisocyanate.

U.S. Pat. Nos. 4,565,857 and 4,839,230 also require the use of isocyanates for attachment of the ethylenically unsaturated moieties to the polymer backbone. This requires the manufacturing process to be moisture free, otherwise the isocyanate moiety reacts with water to form urea by-products which can cause deleterious effects by crystallizing out in the films made from the described resins.

SUMMARY OF THE INVENTION

The present invention provides modified cellulose esters capable of free radical polymerization with other ethylenically unsaturated species when exposed to ultra-violet light. In particular, the invention provides cellulose esters which have been reacted with maleic anhydride to provide maleic or fumeric pendant groups on such modified cellulose esters. The modified cellulose esters can be neutralized with a base to provide a water-disperisble resin suitable for use in waterborne coating compositions. These modified cellulose esters are useful in formulations with other ethylenically unsaturated species and can be cured upon exposure to ultraviolet light in the presence of a photoinitiator to form a hard coating.

DETAILED DESCRIPTION OF THE INVENTION

The present invention provides an ethylenically unsaturated cellulose acetate ester containing carboxylic acid pendant groups attached to the polymer backbone of the formula $$\left[ C_6H_7O_4(O\overset{O}{\underset{\|}{C}}CH_3)_x(R^1)_y(R^2)_z(R^3)_{3-x-y-z} \right]_n$$

wherein:

$R^1$ is independently maleate, fumarate, H, OH, or a mixture thereof;

$R^2$ and $R^3$ are independently

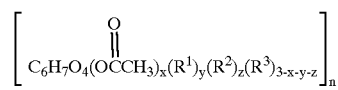

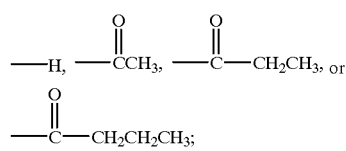

or a mixture thereof;

x is 0.1 to 2.5, y is 0.1 to 2.0, z is 0.1 to 2.5, and n is 30–250, provided that the sum of x, y, and z is in the range of 0.3 to 3.0.

It should be understood from the above structure that the group designated "$C_6H_7O_4$" denotes the residue of alternate halves of an anhydroglucose unit, i.e., a group of the formula

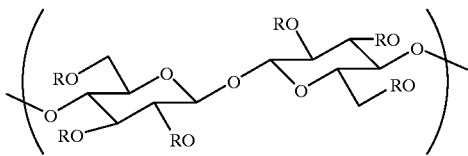

wherein the various R groups are $R^1$, $R^2$, and $R^3$ as shown above.

As used herein, the term "cellulose ester" means an unmodified cellulose ester, and the term "modified cellulose ester" means the modified cellulose ester of the invention which is a cellulose ester having a maleate or fumarate ester pendant group. Such polymers can be rendered water dispersible by reaction with amines.

In a further preferred aspect of the present invention, the modified cellulose esters of the present invention are blended with co-reactive compounds or polymers which possess ethylenic unsaturation which is capable of free radical addition reaction with the maleate or fumarate pendant groups on the modified cellulose esters. Examples of such polymers include epoxy acrylates, urethane acrylates, polyester acrylates, and vinyl acrylates.

The modified cellulose esters of the present invention can be prepared by reacting maleic anhydride and a cellulose ester in the presence of an alkaline earth metal or ammonium salt of a lower alkyl monocarboxylic acid catalyst, and at least one saturated monocarboxylic acid having 2 to 4 carbon atoms, wherein said cellulose ester has a degree of substitution per anhydroglucose unit of residual hydroxyl groups of about 0.1 to 2.0, in the presence of a suitable solvent. The alkaline metal, alkaline earth metal, or ammonium salt of the lower alkyl monocarboxylic acid can be added directly to the reaction mixture or can be generated in situ. The reaction is generally conducted at a temperature of about 50° C. to 120° C., preferably about 70° C. to about 85° C. The reaction time is about 1 to 12 hours. Such solvents would include lower alkyl monocarboxylic acids such as acetic, propionic, isobutyric, and butyric acid, and mixtures thereof. In such reactions, the solvent:cellulose ester ratio by weight varies from about 1:1 to about 20:1, preferably about 2:1 to 5:1.

In the process for preparing the modified cellulose ester, it is preferred that the cellulose ester starting material has a degree of substitution (DS) per anhydro-glucose unit of residual hydroxyl groups of about 0.3 to about 2.0.

The cellulose ester starting materials may be of the acetate, propionate, or butyrate type, or mixed esters thereof. The degree of substitution per anhydro-glucose unit of residual hydroxyl groups for these cellulose esters is in the range of about 0.1 to about 2.0 with about 0.3 to about 1.5 being the preferred range. Typical starting cellulose esters include, but are not limited to; CA 320, CA 398, CAB 381, CAB 551, CAB 553, CAP 482, CAP 504, all commercially available from Eastman Chemical Company, Kingsport, Tenn. Such cellulose ester starting materials typically have a number average molecular weight of between about 10,000 and about 75,000 daltons as determined by gel permeation chromatography using polystyrene standards.

The molar proportions of starting materials used in the manufacturing process of the present invention are those proportions sufficient to result in the desired degree of substitution of the modified cellulose ester to achieve the desired product.

Suitable solvents for preparing the modified cellulose ester of the present invention include, but are not limited to ketones, esters, aliphatic monocarboxylic acids, and chlorinated hydrocarbons. Specific examples include, but are not limited to acetone, 2-butanone, ethyl acetate, propyl acetate, chlorobenzene, methylene chloride, chloroform, acetic acid, and propionic acid. Reactions are typically carried out in about 40 to about 90 wt % solvent solutions based upon the weight of the cellulose ester starting material.

Suitable catalysts useful for preparation of the modified cellulose esters in the present invention include, but are not limited to, amines such as triethylamine, tributylamine, diisopropylamine, and pyridine; alkali metal salts of aliphatic carboxylic such as sodium acetate, potassium acetate, calcium acetate, sodium propionate and potassium propionate; and alkali metal carbonate salts such as sodium carbonate and potassium carbonate. A typical catalyst concentration used is about 25 to about 100 wt % based on the weight of the starting cellulose ester.

In the synthesis processes of the present invention, the reaction is performed under conditions such that the desired modified cellulose ester is formed. Typically the reaction period is about 1 to about 12 hours, preferably about 2 to about 5 hours. The temperature during the reaction is typically about 50° to about 120° C., preferably about 60 to about 80° C.

A preferred process of the present invention is summarized in the following sequential steps:

1. An appropriate cellulose ester starting material is dissolved in a suitable solvent such as reagent grade acetic acid to obtain a solvent solution.
2. The reaction mixture is heated to 65° C.
3. Maleic anhydride is then added and agitated until dissolved.
4. Sodium acetate is added.
5. The reaction mixture is heated to 75° C. for three hours.

In the process of the invention for facilitating isolation of the modified cellulose ester, the nonsolvent is a liquid in which the modified cellulose ester is not soluble. Such nonsolvents include but are not limited to water, isopropyl alcohol, hexane, heptane, and mixtures thereof. The amount of nonsolvent used in the process to precipitate the modified cellulose ester is about 25 to about 100 wt % of nonsolvent based on the total weight of the reaction mixture. It is preferred that such process includes the additional step of separating the precipitated modifier cellulose ester from unprecipitated reaction by-products. Unprecipitated by-products typically include maleic acid, sodium maleate, reaction catalyst, and mixtures thereof.

In a preferred process for isolating and facilitating isolating the modified cellulose ester, after Step 5, the following sequential steps are followed:

6. The reaction mixture is cooled to 50° C. and drowned into water with rapid agitation to precipitate the modified cellulose ester.
7. The modified cellulose ester product is filtered and washed with water to remove unprecipitated reaction by-products. Also, the drowning, filtering, and drying steps may be repeated to further purify the desired product.
8. The water-wet modified cellulose ester is dried at 60° C. in a vacuum oven.

Thus, the present invention provides a process for preparing the modified cellulose esters of the invention, which comprises:

(a) dissolving cellulose acetate, cellulose acetate propionate, or cellulose acetate butyrate in a solvent of the formula

wherein $R^4$ is $C_1$–$C_3$ alkyl to provide a solution;

(b) heating said solution to a temperature of about 50° C. to 120° C.;

(c) treating said solution with maleic anhydride, and a catalyst selected from the group consisiting of an alkaline metal salt, alkaline earth salt, or ammonium salt; and (b) continuing heating at a temperature of about 50° C. to 120° C.

As a further aspect of the invention, there is provided a method for isolating the modified cellulose ester of the present invention wherein said cellulose ester is in unprecipitated form and is in a mixture with reaction by-products and a suitable solvent. This isolation process comprises contacting said mixture with an amount of nonsolvent sufficient to precipitate the desired product. The amount of water used to precipitate the product varies from about 1:4 (parts of water:parts of reaction mixture by weight) to about 5:1, preferably about 0.5:1 to about 1.2:1. The resulting precipitate can be filtered or centrifuged and washed with water, preferably at a temperature of about 10° C. to 90° C.

Alternatively, the modified cellulose esters of the present invention can be prepared by dissolving the cellulose ester in an organic solvent devoid of carboxylic acids and reacting it with maleic anhydride in the presence of a proton acceptor. The reaction is heated and the product precipitated by mixing a nonsolvent with the reaction mixture. The product is then isolated by filtration, washed with water, and dried. In this regard, suitable organic solvents include ketones such as acetone, 2-butanone, 2-pentanone, cyclohexanone; esters such as methyl, ethyl, propyl, iso-propyl, isobutyl, and butyl esters of lower alkyl carboxylic acids; ethers such as diethyl and dibutyl ethers, dialkyl ethers of glycols such as dimethyl, dipropyl, and dibutyl glycols of ethylene and propylene glycols, tetrahydrofuran, and dioxane; dialkyl esters of lower alkyl monocarboxylic acids of ethylene and propylene glycols such as diacetyl, dipropionyl, dibutyrl esters of ethylene and propylene glycols; sulfoxides such as sulfolane, dimethyl sulfoxide and diethyl sulfoxide; dialkylamides of formic, acetic, and propionic acids, N-methyl pyrrolidinone; and chlorinated hydrocarbons such as methylene chloride, chloroform, and chlorobenzene.

The solvent:cellulose ester ratio by weight is generally from about 1:1 to about 20:1, preferably about 2:1 to about 5:1.

The proton acceptor can be, for example, a trialkyl amine such as trimethylamine, triethylamine, tripropylamine, tributylamine, or a mixture thereof; alkyl substituted pyrrolidines and piperidines; dialkyl anilines; pyridine and alkyl substituted pyridines; and inorganic alkaline and alkaline earth carbonates. Such proton acceptors are preferably present in a proportion of about 0.1:1 to about 1:1 (proton acceptor:cellulose ester, by weight).

The temperature for the reaction is about 50° .C to 120° C., preferably about 70° C. to 85° C. The reaction time is generally about 1 to 12 hours. The product can be isolated by adding a reaction mixture-miscible non solvent and isolated by filtration or centrifugation, followed by washing with water, preferably at a temperature of about 10° C. to 90° C. and dried.

Thus, as a further aspect of the invention, there is provided a process for preparing a cellulose acetate ester of the formula

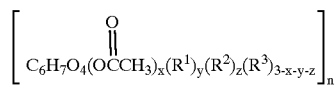

wherein:
$R^1$ is independently maleate, fumarate, H, OH, or a mixture thereof;
$R^2$ and $R^3$ are independently

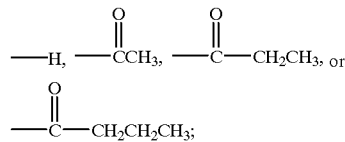

or a mixture thereof;
x is 0.1 to 2.5,
y is 0.1 to 2.0,
z is 0.1 to 2.5, and
n is 30–250, provided that the sum of x, y, and z is in the range of 0.3 to 3.0;
which comprises;

(a) dissolving cellulose acetate, cellulose acetate propionate, or cellulose acetate butyrate in an organic solvent free of carboxylic acids to provide a solution;

(b) heating said solution to a temperature of about 50° C. to 120° C.;

(c) treating said solution with maleic anhydride, in the presence of a proton acceptor.

In the modified cellulose ester of the present invention it is preferred that x is about 0.1 to about 0.4, y is about 0.1 to 0.5, and z is 0.1 to 2.5.

In the undispersed (i.e., solvent-borne) coating composition of the present invention the suitable solvent must be one in which the modified cellulose ester is soluble. Aliphatic hydrocarbons are generally not suitable for this purpose. Typical examples of suitable solvents include, but are not limited to ketones, esters, chlorinated hydrocarbons, aqueous buffer solutions, and mixtures thereof. Specific examples include, but are not limited to acetone, 2-butanone, 2-pentanone, ethyl acetate, propyl acetate, butyl acetate, methyl alcohol, ethyl alcohol, ethylene glycol monoethyl ether, and mixtures thereof. Also, further suitable solvents can be of the ethylenically unsaturated type that, in addition to dissolving the modified cellulose ester, can crosslink with the cellulose upon exposure to UV radiation in the presence of a photoinitiator. Specific examples include, but are not limited to, ethyl(meth)acrylate, methyl (meth)acrylate, hydroxyethyl(meth)acrylate, diethylene glycol diacrylate, trimethylolpropane triacrylate, 1,6 hexanediol di(meth)acrylate, neopentyl glycol di(meth)acrylate, and mixtures thereof.

The amount of suitable solvent in the non-dispersed water-based coating composition of the present invention is that amount sufficient to solubilize the modified cellulose ester. Typically, this amount is about 60 to about 90 weight % of total coating composition, preferably about 65 to about 75 weight %. Mixtures of solvents can be used in the coatings (and processes) of the present invention.

In the water-dispersed coating composition of the present invention the suitable co-solvent must be one that is water miscible and that will solubilize the modified cellulose ester. Typical examples include but are not limited to acetone, 2-butanone, methanol, ethanol, ethylene glycol monoethyl ether, ethylene glycol monopropyl ether, and ethylene glycol monobutyl ether. Typical examples of ethylenically unsaturated solvents include, but are not limited to, 2-ethoxyethyl-(meth)acrylate, polyethylene glycol dimethacrylate, polypropylene glycol mono(meth)acrylate, and mixtures thereof.

Dispersion of the modified cellulose ester of the present invention in water requires about 25 to about 100% neutralization of the pendant carboxylate groups with an aliphatic amine. Typical aliphatic amines include but are not limited to piperidine, 4-ethyl-morpholine, diethanolamine, triethanolamine, ethanol-amine, tributylamine, dibutylamine, and ammonia.

The amount of suitable aqueous solvent in the dispersed coating composition of the present invention is 50 to about 90 wt %, preferably about 75 to about 90 wt % of the total coating composition.

The coating compositions of the present invention optionally contain a photoinitiator. The amount of photoinitiator is typically about 2 to about 7 wt % based on the weight of the non-volatile content of the coating composition; preferably about 3 to about 5 wt %. Suitable photoinitiators include, but are not limited to, acetophenone/ and benzophenone/tertiary amine combinations, organic peroxides, benzoin and its ethers, benzil and benzil ketals. A preferred photoinitiator is IRIGACURE® 651 Photocuring Agent (2,2-dimethoxy-2-phenylacetophenone), available from Ciba-Geigy. If a UV curable composition is desired, a photoinitiator must be present. In the case of electron beam curing, the photoinitiator may be omitted. Further details regarding such photoinitiators and curing procedures can be found in U.S. Pat. No. 5,109,097, incorporated herein by reference.

The coating composition may contain other formulation additives which contribute to the non-volatile content of the composition. Such additives include, for example, leveling agents, antifoamants, and the like. Such additives may be present in an amount from about 0.1 to about 5 wt % of total coating composition, preferably about 0.1 to about 1.0 wt %.

As a further aspect of the present invention there is provided a curable composition as described above, further comprising one or more leveling, rheology, and flow control agents such as silicones, fluorocarbons or cellulosics; flatting agents; pigment wetting and dispersing agents; surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewcides; corrosion inhibitors; thickening agents; or coalescing agents.

Specific examples of such additives can be found in *Raw Materials Index,* published by the National Paint & Coatings Association, 1500 Rhode Island Avenue, N.W., Washington, D.C. 20005.

Examples of flatting agents include synthetic silica, available from the Davison Chemical Division of W. R. Grace & Company under the trademark SYLOID®; polypropylene, available from Hercules Inc., under the trademark HERCOFLAT®; synthetic silicate, available from J. M Huber Corporation under the trademark ZEOLEX®.

Examples of dispersing agents and surfactants include sodium bis(tridecyl) sulfosuccinnate, di(2-ethyl hexyl) sodium sulfosuccinate, sodium dihexylsulfosuccinnate, sodium dicyclohexyl sulfosuccinnate, diamyl sodium sulfosuccinate, sodium diisobutyl sulfosuccinate, disodium iso-decyl sulfosuccinnate, disodium ethoxylated alcohol half ester of sulfosuccinnic acid, disodium alkyl amido polyethoxy sulfosuccinnate, tetra-sodium N-(1,2-dicarboxyethyl)-N-oxtadecyl sulfosuccinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkyl amine salt of an unsaturated fatty acid, all available from BYK Chemie U.S.A. under the trademark ANTI TERRA®. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide.

Several proprietary antifoaming agents are commercially available, for example, under the trademark BRUBREAK of Buckman Laboratories Inc., under the BYK® trademark of BYK Chemie, U.S.A., under the FOAMASTER® and NOPCO® trademarks of Henkel Corp./Coating Chemicals, under the DREWPLUS® trademark of the Drew Industrial Division of Ashland Chemical Company, under the TROYSOL® and TROYKYD® trademarks of Troy Chemical Corporation, and under the SAG® trademark of Union Carbide Corporation.

Examples of fungicides, mildewcides, and biocides include 4,4-dimethyloxazolidine, 3,4,4-trimethyloxazolidine, modified barium metaborate, potassium N-hydroxy-methyl-N-methyldithiocarbamate, 2-(thiocyanomethylthio) benzothiazole, potassium dimethyl dithiocarbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Examples of U.V. absorbers and U.V. light stabilizers include substituted benzophenone, substituted benzotriazole, hindered amine, and hindered benzoate, available from American Cyanamide Company under the tradename Cyasorb UV, and available from Ciba Geigy under the trademark TINUVIN, and diethyl-3-acetyl-4-hydroxy-benzyl-phosphonate, 4-dodecyloxy-2-hydroxy benzophenone, and resorcinol monobenzoate.

Such paint or coating additives as described above form a relatively minor proportion of the enamel composition, preferably about 0.05 weight % to about 5.00 weight %.

To prepare the coated articles of the present invention, the modified cellulose ester of the present invention is applied to a substrate and then is cured (i.e., polymerized and crosslinked), in the presence of IRGACURE® 651 benzil ketal, IRGACURE® 184 benzil, or DAROCURE® 1173 benzil, by an amount of ultraviolet radiation sufficient to effect the desired degree of curing. The substrate can be, for example, wood; plastic; metal such as aluminum or steel; cardboard; glass; cellulose acetate butyrate sheeting; and various blends containing, for example, polypropylene, polycarbonate, polyesters such as polyethylene terephthalate, acrylic sheeting, as well as other solid substrates.

The coating composition of the present invention is preferably further comprised of auxiliary polymerizable monomers and/or oligomers such as, but not limited to, vinyl acetate, N-vinyl pyrrolidone methyl(meth)acrylate, butyl (meth)acrylate, 2-hydroxyethyl (meth)acrylate, neopentylglycol di(meth)acrylate, triethyleneglycol di(meth)acrylate, trimethylolpropane triacrylate, (meth)acrylated urethanes such as EBECRYL® 220, SARTOMERO CN 964 and CN 965; (meth)acrylated epoxies such as SARTOMER® CN 104; and (meth)acrylated polyesters and polyethers.

The curing of the modified cellulose esters of the present invention can be carried out in the liquid or solid state (i.e., as a dry film).

Depending upon the thickness of the coating (film), product formulation, photoinitiator type, radiation flux, and source of radiation, exposure times to ultra-violet radiation of about 0.5 to about 10 seconds are typically required for curing.

The coating on the coated article of the present invention typically has a solvent resistance of at least 100 double rubs using ASTM Procedure D-3732; preferably a solvent resistance of at least about 200 double rubs. Such coating also typically has a pencil hardness of greater than or equal to F using ASTM Procedure D-3363; preferably a pencil hardness of greater than or equal to H.

The modified cellulose esters are also useful in fingernail polish compositions.

The general formulation for UV-curable fingernail polishes containing modified cellulose esters of the present invention is as follows:

| | |
|---|---|
| 5–50% | modified cellulose ester as the major film former |
| 10–90% | copolymerizable monomer |
| 0–10% | modifying resin |
| 0–25% | plasticizer |
| 0–5% | pigment |
| 2–7% | photoinitiator |
| 0–90% | solvents |

Typical copolymerizable monomers are (meth)acrylic acid, crotonic acid, maleic acid, fumaric, itaconic acid and their anhydrides, cyanoacrylic; esters of (meth)-acrylic acid such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, benzyl, and substituted phenoxyl, behenyl; di(meth)acrylate esters of ethylene and propylene glycols, 1,3-butylene glycol, 1,4-butanediol, diethylene and dipropylene glycols, triethylene and tripropylene glycols, 1,6-hexanediol, neopentyl glycol, polyethylene glycol, and polypropylene glycol, ethoxylated bisphenol A, propoxylated neopentyl glycol; tri(meth)acrylate esters of tris-(2-hydroxyethyl)isocyanurate, trimethylolpropane,pentaerythritol, glycerol, ethoxylated and propoxylated glycerol; tetra(meth)acrylate esters of pentaerythritol; acrylonitrile, vinyl acetate, vinyl toluene, styrene, N-vinylpyrrolidinone, and alpha-methylstyrene.

Typical modifying resins include homopolymers and copolymers of (meth)acrylic acid; alkyl esters of (meth) acrylic acid such as allyl, methyl, ethyl, n-propyl, isopropyl, butyl, tetrahydrofurfuryl, cyclo-hexyl, isobornyl, n-hexyl, n-octyl, isooctyl, 2-ethyl- hexyl, lauryl, stearyl, benzyl; (meth)acrylated urethane, epoxy, and polyester resins, silicone acrylates.

Typical (meth)acrylated epoxy resins would be ACTILANE 7220 TP, ACTILANE 72, and ACTOCRYL 10020 A from Anchor Chemical (UK); CRODAMER UVE series from Croda; CRAYNOR CN104 and 114 from Cray Valley; DEREKANE 200 from Dow Europe S.A.; EBECRYL 200, 220, and 3700 from Radcure Specialties; and PHOTOMER 3015 and 3016 from Henkel.

Typical (meth)acrylated urethanes are ACTILANE 20, 23, and 27 from Anchor Chemical (UK); CRAYNOR CN 934, 946, 960, and 965 from Cray Valley; Daicel SR 6010, 6012, 6022, and 6023 from Daicel Chemical Industries; EBECRYL 230, 270, 1290, 5129, and 8804 by Radcure Specialties; PHOTOMER 6008, 6010, 6338, and 6264 by Henkel.

Typical (meth)acrylated polyester resins would be EBECRYL 657, 810, 830, and 1657 from Radcure Specialties; LAROMER LR 8799 and 8800 by BASF; and PHOTOMER 5007, 5018, and 5029 from Henkel.

Typical silicone (meth)acrylates include EBECRYL 350 and 1360 from Radcure Specialties; PHOTOMER 7020 from Henkel; TEGO 704, 705, 725, and 726 from Goldschmidt AG; and WACKER F-737 by Wacker Silicones.

Typical plasticizers include alkyl esters of phthalic acid such as dimethyl phthalate, diethyl phthalate, dipropyl phthalate, dubutyl phthalate, and dioctyl phthalate; citrate esters such as triethyl citrate and tributyl citrate; triacetin and tripropionin; and glycerol monoesters such as MYVEROL 18-04, 18-07, 18-92 and 18-99 from Eastman Chemical Company.

Typical solvents include lower molecular weight alcohols such as ethanol, propanol, isopropyl alcohol, butanol, pentanol, hexanol, and 2-ethylhexanol; glycols such as ethylene and propylene glycols; ketones such as acetone, 2-butanone, and 2-pentanone; esters such as methyl and ethyl acetate, isopropyl acetate, butyl and isobutyl acetate, ethylene glycol diacetate, propylene glycol diacetate.

Typical photoinitiators include benzoin and benzoin ethers such as ESACURE B0, EB1, EB3, and EB4 from Fratelli Lamberti; VICURE 10 and 30 from Stauffer; benzilketals such as IRGACURE 651 from Ciba Geigy, Uvatone 8302 by Upjohn; alpha, alpha-dialkoxyacetophenone derivatives such as DEAP and UVATONE 8301 from Upjohn; alpha-hydroxyalkylphenones such as IRGACURE 184 from Ciba Geigy; DAROCUR 116, 1173, and 2959 by Merck; mixtures of benzophenone and tertiary amines.

A specific formulation for a UV-curable fingernail polish based on a modified cellulose ester of the present invention is the following:

| | |
|---|---|
| 25 parts | modified cellulose ester (major film former) |
| 12 parts | ethyl acetate |
| 24 parts | butyl acetate |
| 8 parts | acrylated urethane resin (EBECRYL 220 from Radcure Industries) |
| 22 parts | tripropyleneglycol diacrylate |
| 5 parts | N-vinylpyrrolidone |
| 4 parts | IRGACURE 651 photoinitiator (Ciba Geigy) |

EXPERIMENTAL SECTION

Example 1—Preparation of CAP 504 Cellulose Acetate Propionate Grafted with TMI® Isocyanate and Methacrylate Groups A solution is made consisting of 100 g of dry CAP 504-0.2 (available from Eastman Chemical Company—cellulose acetate propionate—approximately 42.5 weight percent propionyl content, 0.6 weight percent acetyl content, and 5.0 weight percent hydroxyl content) and 500 g of urethane-grade propyl acetate. The solution is brought to reflux and approximately 100 g of propyl acetate is distilled out to azeotropically dry the cellulose ester. The solution is cooled to 50° to 60° C. and 0.5 g of dibutyltin dilaurate catalyst and 33 g of TMI® (meta-isopropenyl-2,2'-dimethyl benzyl isocyanate, available commercially from Cytec) are added. The reaction mixture is refluxed until the —NCO absorption in the infrared spectrum of the reaction mixture is no longer discernible from the baseline. The reaction mixture is cooled to 30° C. The following are added: 26 grams of triethylamine, 0.5 g hydroquinone monomethyl ether, and 40 g of methacrylic anhydride. The reaction mixture is refluxed for 6 hours, cooled to 30° C., and drowned into 1 liter of hexane with high speed agitation. The cellulose ester is filtered and dried at 60° C.

The analysis of the cellulose ester product by nuclear magnetic resonance showed the degree of substitution per anhydroglucose for propionate, TMI moiety, and methacrylate to be 2.0, 0.6 and 0.1, respectively.

Example 2—Preparation of CAP 504-maleate (Sample 4)

In a 5-gallon sigma blade mixture are placed 7300 g reagent grade acetic acid and 2500 g of CAP 504-0.2, commercially available from Eastman Chemical Company, Kingsport, Tenn. The reaction mixture is heated to 65° C. and agitated until all the cellulose ester dissolves. Then 1250 g of maleic anhydride is added and agitated at 65° C. until a clear solution is obtained, after which 1250 g of anhydrous sodium acetate is added. The reaction mixture is heated at 75° C. for three hours and then cooled to 50° C., where upon it is drowned into 9000 g of water with high speed agitation to precipitate the modified cellulose ester product. The precipitated cellulose ester is collected by filtration and then washed with 15,000 g of water. The water-wet modified cellulose ester product is then dried in a vacuum oven at 60° C. to a moisture content of less than 2%. Analysis by nuclear magnetic resonance showed the degree of substitution per anhydroglucose unit for acetate, propionate and maleate to be 0.40, 2.09 and 0.39, respectively.

Example 3—Preparation of CAB 553-0.4 (Celluose Acetate Butyrate) Maleate (Sample 6)

In a 5-gallon sigma blade mixture are placed 7300 g reagent grade acetic acid and 2500 g of CAB 553-0.4, commercially available from Eastman Chemical Company, Kingsport, Tenn. (cellulose acetate butyrate having a butyryl content of 46 weight percent, an acetyl content of 2 weight percent, and a hydroxyl content of 4.8 weight percent). The reaction mixture is heated to 65° C. and agitated until all the cellulose ester dissolves. Then 1250 g of maleic anhydride is added and agitated at 65° C. until a clear solution is obtained, after which 1250 g of anhydrous sodium acetate is added. The reaction mixture is heated at 75° C. for three hours and then cooled to 50° C., where upon it is drowned into 9000 g of water with high speed agitation to precipitate the modified cellulose ester product. The precipitated cellulose ester product is collected by filtration and then washed with 15,000 g of water. The water-wet modified cellulose ester is then dried in a vacuum oven at 60° C. to a moisture content of less than 2%. Analysis by nuclear magnetic resonance showed the degree of substitution (DS) per anhydroglucose unit for acetate, butyrate, and maleate to be 0.15, 2.1, and 0.41, respectively.

In similar fashion additional samples of modified cellulose esters with a variety of DS of substituents were prepared and are given in the Table 1 below:

TABLE 1

| | Cellulose Ester Maleates | | | | | |
|---|---|---|---|---|---|---|
| Sample | 1 | 2 | 3 | 4 | 5 | 6 |
| Acetate | 1.82 DS | 0.22 | 0.22 | 0.40 | 0.20 | 0.15 |
| Propionate | — | 2.20 | 2.10 | 2.09 | 2.05 | — |
| Butyrate | — | — | — | — | — | 2.0 |
| Maleate | 0.32 | 0.0.10 | 0.25 | 0.39 | 0.46 | 0.41 |

Coating Compositions of Modified Cellulose Ester Samples

Solutions of modified cellulose esters prepared as described hereinbefore (Samples 1–6 and as in Example 1) were dissolved in butyl acetate with a concentration of 20% by weight of modified cellulose ester containing 5% by weight of photoinitiator (IRGACURE® 651 by Ciba Geigy) and 10% by weight of EBECRYL® 220, an hexacrylated urethane oligomer as a crosslinking agent.

Coating of Substrates

Samples 1–6 and the modified cellulose ester prepared in Example 1 were used to coat a variety of substrates such as glass, wood, metal, and plastics. For each type, the coating operation was the same. The substrate was coated with the above formulation using a knife blade. The wet film thickness was about 10 mil. The solvent was evaporated to give a clear non-tacky film with a thickness of approximately 1 mil. Prior to exposure to UV radiation, each film was readily soluble in organic solvents.

Film Curing

The dried film was exposed to UV radiation from a 200 watt per inch medium pressure mercury vapor lamp housed in an American Ultraviolet Company instrument using a belt speed of 25 ft. per minute. Two to five passes under the lamp resulted in a crosslinked coating with maximum hardness and solvent resistance.

Coating Evaporations

Pencil hardness (ASTM D3363), solvent resistance by the methyl ethyl ketone double-rub test, and solubility in acetone were measured for each film before and after exposure to UV radiation. Data for control resins are also included.

The pencil hardness scale is in order of increasing hardness:

| 5B | 4B | 3B | 2B | B | HB | F | H | 2H | 3H | 4H | 5H |
|---|---|---|---|---|---|---|---|---|---|---|---|

The methyl ethyl ketone (MFK) double rub test is carried out by saturating a piece of cheesecloth with methyl ethyl ketone, and with moderate pressure, rubbing the coating back and forth. The number of double rubs is counted until the coating is removed. This test is in accordance with ASTM Procedure D-3732.

The acetone solubility test is carried out by immersing a dry, pre-weighed sample of the film in acetone for 48 hours at 25° C. The film is removed, dried for 16 hours at 60° C.

in a forced-air oven, and reweighed. The weight percent of the insoluble film remaining is calculated from the data.

COATING EVALUATIONS
Before Irradiation

| Resin Description | Pencil Hardness | MEK Rubs | Acetone Insolubles |
|---|---|---|---|
| CA 320S (Control)[1] | F | <10 | Dissolved |
| CAP 504 (Control)[1] | HB | <10 | Dissolved |
| CAB 553 (Control)[1] | 2B | <10 | Dissolved |
| CAP-TMI-MA (Ex. 1) | F | <10 | Dissolved |
| CA Mal (0.32 DS) (Sample 1) | F | <10 | Dissolved |
| CAP Mal (0.10 DS) (Sample 2) | F | <10 | Dissolved |
| CAP Mal (0.25 DS) (Sample 3) | F | <10 | Dissolved |
| CAP Mal (0.39 DS) (Sample 4) | F | <10 | Dissolved |
| CAP Mal (0.46 DS) (Sample 5) | F | <10 | Dissolved |
| CAB Mal (0.41 DS) (Sample 6) | HB | <10 | Dissolved |

[1]Not formulated

After Irradiation

| Resin Description | Pencil Hardness | MEK Rubs | Acetone Insolubles |
|---|---|---|---|
| CA 320S (Control)[1] | F | <10 | Dissolved |
| CAP 504 (Control)[1] | HB | <10 | Dissolved |
| CAB 553 (Control)[1] | 2B | <10 | Dissolved |
| CAP-TMI-MA (Ex. 1) | H | <200 | 9096 |
| CA Mal (0.32 DS) (Sample 1) | H/2H | <200 | 9496 |
| CAP Mal (0.10 DS) (Sample 2) | F | <98 | 4296 |
| CAP Mal (0.25 DS) (Sample 3) | H | <200 | 9096 |
| CAP Mal (0.39 DS) (Sample 4) | H/2H | <200 | 9496 |
| CAP Mal (0.46 DS) (Sample 5) | H | <200 | 9196 |
| CAB Mal (0.41 DS) (Sample 6) | HF | <200 | 9296 |

[1]Not formulated

Example 4—Dispersion of Modified Cellulose Ester (Sample 3) in Water

Into a container with an agitator are placed 15 g of CAP 504-0.2 maleate (0.25 DS maleate, 2.10 DS propionate, 0.25 DS acetate, with acid no. of 45 mg KOH/g of polymer) and 30 g of ethylene glycol monobutyl ether. The contents are agitated until a clear solution is obtained and then 50% of the carboxyl groups are neutralized by adding 0.37 g of ethanolamine. After agitation for 5 minutes, 55 g of water is slowly added with agitation to generate a dispersion suitable for coating applications.

The formula below is useful for calculating the amount of amine to add for neutralization to any degree of the carboxylic acid pendent groups.

$$\text{wt of amine} = \frac{(\text{wt. of cellulose ester, g})(\text{acid no. of cellulose ester})(\text{mw of amine})}{56,100} \times \frac{(\% \text{ carboxyl neutralization})}{100}$$

Example 4—Attempted Dispersion of CAP 504-0.2 Grafted with TMI® and Methacrylate Groups Into a container with an agitator are placed 15 g of CAP 504-0.2 grafted with TMI® and methacrylate groups prepared in Example 1 above and 30 g of ethylene glycol monobutyl ether. The mixture is stirred until a clear solution is obtained, whereupon 0.37 g of ethanolamine are added followed by 55 g of water. Upon addition of water the modified cellulose ester precipitates and does not form a dispersion suitable for coating applications.

Example 5—Formulation and use of modified cellulose Ester as a Protective Wood Coating Modified cellulose ester (Sample 3) was used in the following formulations:

| Component | Parts by Wt. |
|---|---|
| Modified cellulose ester (Sample 3) | 16.4 |
| Methyl amyl ketone | 32.6 |
| Methyl propyl ketone | 15.5 |
| TECSOL® C 95 (ethyl alcohol, available from Eastman Chemical Company) | 28.2 |
| EBECRYL® 6700 (aromatic urethane diacrylate diluted with 15% of 1,6-hexanediol diacrylate-available from Radcure Specialties) | 3.6 |
| EBECRYL® 220 (a multifunctional aromatic urethane acrylate containing and acrylated polyol diluent) | 2.7 |
| IRGACURE® 651 | 1.0 |

The Brookfield viscosity at 25° C. was 79 cP.
The % solids content was 23.7%.

Application to and Curing of Wood Panels

Pine wood panels were first coated with a CAB/acrylic sealer, dried, and sanded with 32-grit sandpaper. Two coats of the above formulation were spray-applied and allowed to dry for 30 minutes. The panels were exposed in three passes to UV radiation from two 200 watt per inch medium pressure mercury vapor lamps housed in an American Ultraviolet Company instrument using a belt speed of 20 ft. per minutes.

Evaluation of Cured Coating on Wood Panels

The following properties were measured using standard test procedures:

| Property | Value | ASTM Method |
|---|---|---|
| Print Resistance | 5 lb/ln$^2$ @ 50° C. | D 2091-87 |
| Hardness | 16.0 Knoops | D 1474 |
| Cold-check Resistance | 21 cycles passed | D 12-11-87 |
| Acetone Double Rubs | >200 rubs | D 3732 |
| Stain Resistance | Results given below: | D 3023-88 |

| Staining Agent | Result |
|---|---|
| Ammonia | NS |
| Bourbon | NS |
| Hydrochloric acid, 2% | NS |
| KOH, 10% | S |
| Mustard | NS |
| Red wine | NS |
| Shoe Polish | NS |
| Isopropyl alcohol, 70% | NS |
| Pine oil cleaner | NS |
| Nail polish remover | NS |
| Iodine | NS |

Example 6—Use of Modified Cellulose Ester in "100% Solids" UV-Curable Coating Formulation Sample 3 was used in the following formulation to demonstrate its efficacy in "solventless" UV-cure formulations:

| Component | Parts by Wt. |
| --- | --- |
| Modified cellulose ester (Sample 3) | 8 |
| Roskydal ® 300 (Bayer) | 43 |
| 1,6 Hexanediol diacrylate | 28 |
| 2-Hydroxyethyl methacrylate | 9 |
| EBECRYL ® 220 | 7 |
| IRGACURE ® 184 (Ciba Geigy) | 5 |

We claim:

1. An ethylenically unsatuarted cellulose acetate ester of the formula $$[C_6H_7O_4(OC(O)CH_3)_x(R^1)_y(R^2)_z(R^3)_{3-x-y-z}]_n$$

wherein:

$R^1$ is independently maleate having carboxylic acid pendant groups, fumarate having carboxylic acid pendant groups, or a mixture thereof;

$R^2$ and $R^3$ are independently

—H, —C(O)CH$_3$, —C(O)CH$_2$CH$_3$, or —C(O)CH$_2$ CH$_2$ CH$_3$; or a mixture thereof;

x is 0.1 to 2.5, y is 0.1 to 2.0, z is 0.1 to 2.5, and n is 30–250, provided that the sum of x, y, and z is in the range of 0.3 to 3.0.

2. The cellulose acetate ester of claim 1, wherein x is 0.1 to 0.4, y is 0.1 to 0.5, and z is 0.1 to 2.5.

3. The cellulose acetate ester of claim 1, wherein R1 is maleate having carboxylic acid pendant groups.

4. The cellulose acetate ester of claim 1, wherein R1 is fumarate having carboxylic acid pendant groups.

* * * * *